(12) United States Patent
Chodorowski et al.

(10) Patent No.: US 6,607,713 B1
(45) Date of Patent: Aug. 19, 2003

(54) METHOD FOR IMPROVING UV RADIATION STABILITY OF PHOTOSENSITIVE SUNSCREEN FILTERS

(75) Inventors: Sandrine Chodorowski, Senlis (FR); Francis Xavier Quinn, Paris (FR); Clément Sanchez, Gif-sur-Yvette (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/857,280

(22) PCT Filed: Sep. 28, 2000

(86) PCT No.: PCT/FR00/02688

§ 371 (c)(1), (2), (4) Date: Aug. 21, 2001

(87) PCT Pub. No.: WO01/24762

PCT Pub. Date: Apr. 12, 2001

(30) Foreign Application Priority Data

Oct. 1, 1999 (FR) .............................................. 99 12320

(51) Int. Cl.[7] .......................... A61K 7/42; A61K 7/44; A61K 7/00; A61K 9/66; A61K 9/50
(52) U.S. Cl. .......................... 424/59; 424/60; 424/401; 424/451; 424/455; 424/489; 424/490
(58) Field of Search .......................... 424/59, 60, 401, 424/451, 455, 489, 490; 501/12, 32, 53

(56) References Cited

U.S. PATENT DOCUMENTS 5,902,569 A    5/1999   Oshima et al.
6,159,453 A  * 12/2000  Avnir et al. .................. 424/59

FOREIGN PATENT DOCUMENTS

| JP | 2251240 | 10/1990 |
|---|---|---|
| JP | 19980242486 | 2/2000 |
| WO | WO95/34624 | 12/1995 |
| WO | WO98/31333 | 7/1998 |
| WO | WO98/44906 | 10/1998 |
| WO | WO00/09652 | 2/2000 |
| WO | WO 00/71084 | 11/2000 |
| WO | WO 00/72806 | 12/2000 |

* cited by examiner

*Primary Examiner*—Shelley A. Dodson
(74) *Attorney, Agent, or Firm*—Pillsbury Winthrop LLP

(57) ABSTRACT

The invention relates to a process for improving the stability with respect to UV radiation of a photosensitive sunscreen agent, comprising the incorporation of said screening agent in a material prepared by the sol-gel route from at least one silicon alkoxide and from at least one surfactant. It is also targeted at a photostable material which comprises the combination of a photosensitive sunscreen agent and of a photostabilizing material prepared by the sol-gel route including at least one silicon alkoxide and at least one nonionic surfactant and at a cosmetic and/or dermatological composition comprising, in a cosmetically and/or dermatologically acceptable vehicle, an effective amount of a photostable material. This cosmetic and/or dermatological composition is intended mainly for protecting the skin and/or keratinous substances against ultraviolet radiation.

50 Claims, No Drawings

METHOD FOR IMPROVING UV RADIATION STABILITY OF PHOTOSENSITIVE SUNSCREEN FILTERS

CROSS REFERENCE TO RELATED APPLICATIONS

This is a U.S. national phase of International Patent Application No. PCT/FR00/02688, filed Sep. 28, 2000, which claims priority to French Patent Application No. 99/12320, filed Oct. 1, 1999.

The present invention relates to a process for improving the stability with respect to UV radiation of a sunscreen agent which is sensitive to UV radiation. It also relates to a photostable material and to a cosmetic and/or dermatological composition comprising such a material.

It is known that light radiation with wavelengths of between 280 nm and 400 nm makes possible browning of the human epidermis and that rays with wavelengths of between 280 nm and 320 nm, known under the name of UV-B radiation, result in erythemas and cutaneous burns which can be harmful to the development of natural tanning; this UV-B radiation therefore has to be screened out.

It is also known that UV-A rays with wavelengths of between 320 and 400 nm, which result in browning of the skin, are capable of bringing about a detrimental change in the latter, in particular in the case of sensitive skin or of skin continually exposed to solar radiation. UV-A rays are more penetrating than UV-B rays and result in particular in a loss of elasticity of the skin and the appearance of wrinkles, leading to premature aging. They promote the triggering of the erythemal reaction or enhance this reaction in some subjects and can even be the cause of phototoxic or photoallergic reactions. It is therefore desirable also to screen out UV-A radiation.

Thus, with the aim of providing protection of the skin and keratinous substances against UV radiation, use is generally made of antisun compositions comprising screening agents which are active in the UV-A region and screening agents which are active in the UV-B region.

From this perspective, a well known and particularly advantageous family of screening agents which are active in the UV-A region is composed of dibenzoylmethane derivatives and in particular 4-t-butyl-4'-methoxydibenzoylmethane, sold by Hoffmann-Laroche under the name <<Parsol® 1789". Likewise, a particularly advantageous family of screening agents which are active in the UV-B region is currently composed of cinnamic acid derivatives and in particular 2-ethylhexyl p-cinnamate, sold by Hoffmann-Laroche under the name <<Parsol® MCX".

In point of fact, sunscreen agents such as Parsol® 1789 and Parsol® MCX exhibit a major problem of sensitivity to UV radiation. This is because it is found that dibenzoylmethane derivatives are products which are relatively sensitive to ultraviolet radiation. They exhibit an unfortunate tendency to decompose more or less rapidly under the action of the latter. Thus, this photochemical sensitivity of dibenzoylmethane derivatives in the face of the ultraviolet radiation to which they are by nature intended to be subjected does not make it possible to guarantee constant protection during prolonged exposure to the sun, so that the user is subjected to the restriction of having to make repeated applications at regular and frequent intervals of time in order to obtain effective protection of the skin against UV radiation. The same applies for cinnamic acid derivatives.

Consequently, attempts have been made to reduce the sensitivity to UV radiation of these screening agents (denoted in the continuation of the present document by photosensitive screening agents) but numerous formulating problems have been encountered. For example, a specific photosensitive screening agent may not be able to be formulated with some other active products, requiring on each occasion the development of a new formulation. Likewise, a photosensitive screening agent may not be able to be formulated with some other screening agents, for example Parsol® 1789 (UV-A screening agent) and Parsol® MCX (UV-B screening agent). Furthermore, these photosensitive sunscreen agents have a protective effect which is necessarily limited over time and, in order to compensate for their sensitivity to UV radiation, it is necessary to include large amounts thereof in the formulations without this being sufficient, however, to solve the problem.

This problem of sensitivity to UV radiation of sunscreen agents is well known to the person skilled in the art. In particular, Patent Application PCT No. WO 98/31333 discloses the incorporation of a sunscreen agent in a material prepared by the sol-gel route but this exhibits the following major disadvantages. The inclusion of the screening agent in an effective amount in a material such as is disclosed in this document results in significant incompatibilities as regards stability with respect to UV radiation.

The Applicant Company has found, surprisingly, that, by combining a photosensitive sunscreen agent with a material prepared by the sol-gel route comprising at least one silicon alkoxide and at least one surfactant, a material is obtained which has an improved stability with respect to UV radiation. The photostable material and the cosmetic and/or dermatological compositions which comprise an effective amount of this material are able to form films with a pleasant feel and exhibit very good persistence toward pure or salt water and toward polar and nonpolar cosmetic oils.

A subject matter of the present invention is thus a process for improving the stability with respect to UV radiation of a photosensitive screening agent which comprises the incorporation of the screening agent in a material prepared by the sol-gel route from at least one silicon alkoxide and from at least one surfactant.

Another subject matter is a photostable material comprising a photosensitive screening agent combined with a photostabilizing material prepared by the sol-gel route from at least one silicon alkoxide and from at least one surfactant.

Another subject matter of the present invention is a cosmetic and/or dermatological composition comprising an effective amount of a photostable material according to the invention.

Other characteristics, aspects and advantages of the invention will become even more clearly apparent on reading the description and various examples which follow.

According to the present invention, the process for improving the stability with respect to UV radiation of a photosensitive sunscreen agent comprises the incorporation of said screening agent in a material prepared by the sol-gel route including:

(a) at least one silicon alkoxide chosen from those corresponding to one of the following formulae:

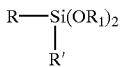

(IV)

in which:
R₁ represents a linear or branched $C_{1-30}$, preferably $C_{1-6}$, alkyl group;
R and R', independently of one another, represent a linear or branched alkyl group, a cycloalkyl group or an aryl group which is substituted or unsubstituted, it being possible for said R and R' groups to additionally comprise a cosmetically or dermatologically active group; R>> represents a linear or branched alkylene group, a cycloalkylene group or an arylene group which is substituted or unsubstituted, it being possible for said R>> group to additionally comprise a cosmetically or dermatologically active group;
(b) at least one solvent,
(c) at least one surfactant, and
(d) water.

Mention may be made, among the cosmetically or dermatologically active groups which can be carried by the R, R' and R>> groups, of, for example, a coloring group, a photochromic group, a group which promotes adhesion to keratinous substances, such as groups of phosphate, phosphonate, phosphonic acid, amide, urethane, ureido, hydroxyl, carboxyl, thiol, amino acid or polypeptide type, a group for combating free radicals or a vitamin-carrying group.

Preference is very particularly given, among the silicon alkoxides defined above, to tetraethoxysilane and methyltriethoxysilane.

The surfactants which can be used in the present invention are all the compounds which are chemically compatible with the silicon alkoxide, the solvent and the photosensitive sunscreen agent.

The surfactant is preferably a nonionic surfactant generally chosen from polyethoxylated, polypropoxylated or polyglycerolated fatty alcohols, alkylphenols or acids with a fatty chain comprising from 6 to 32 carbon atoms, preferably from 8 to 18 carbon atoms, the number of ethylene oxide or propylene oxide groups being between 2 and 100, preferably between 2 and 50, and the number of glycerol groups being between 2 and 30.

Mention may also be made, as nonionic surfactant, of copolymers of ethylene oxide and of propylene oxide; condensates of ethylene oxide and of propylene oxide with fatty alcohols; polyethoxylated fatty amides preferably having 2 to 30 mol of ethylene oxide; polyglycerolated fatty amides preferably comprising 1 to 5 glycerol groups and in particular 1.5 to 4; polyethoxylated fatty amines preferably having 2 to 30 mol of ethylene oxide; sorbitan fatty acid esters ethoxylated with 2 to 30 mol of ethylene oxide; sucrose fatty acid esters, polyethylene glycol fatty acid esters, alkylpolyglucosides, carbamate or amide derivatives of N-alkylglucamines, aldobionamides or amine oxides, such as alkylamine or N-(acylamidopropyl)morpholine oxides.

Preference is very particularly given, among the surfactants mentioned above, to the use of a polyethoxylated 4-(1,1,3,3-tetramethylbutyl)phenol. The latter is sold under the name of Triton® X100 by Rohm & Haas.

The amount of surfactant used in the present invention will depend on its solubility in the alkoxide/solvent/water mixture. The ratio by weight of the surfactant to the silicon alkoxide generally varies from 0.01% to 99%, preferably from 1% to 60%.

Mention may be made, among photosensitive sunscreen agents which can be used according to the invention, of dibenzoylmethane derivatives and cinnamic acid derivatives. Mention may be made, among dibenzoylmethane derivatives, without being restricted thereto, of:

2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4,4'-dimethoxydibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane,
2,6-dimethyl-4-tert-butyl-4'-methoxydibenzoylmethane.

Preference is very particularly given, among the dibenzoylmethane derivatives mentioned above, according to the present invention, to 4-tert-butyl-4'-methoxydibenzoylmethane, available commercially under the name Parsol® 1789 from Hoffmann-Laroche.

Use may be made, as other photosensitive screening agent, of cinnamic acid derivatives chosen from those corresponding to the following general formula:

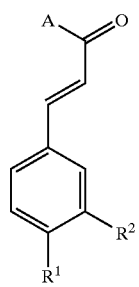

in which:
A represents:
an $OR^3$ group, $R^3$ being chosen from a hydrogen atom, a phytyl or benzyl group, a saturated or unsaturated and linear, branched or cyclic $C_1$–$C_{18}$ alkyl group, an alkali metal or an alkaline earth metal salt [sic] or an ammonium ion [sic], or
an $NHR^4$ group, $R^4$ being chosen from a hydrogen atom, a phytyl or benzyl group or a saturated or unsaturated and linear, branched or cyclic $C_1$–$C_{18}$ alkyl group;
$R^1$ represents a group chosen from H, OH, $C_1$–$C_6$ alkoxy, preferably methoxy, or a saturated or unsaturated and linear, branched or cyclic $C_1$–$C_{18}$ alkyl group;
$R^2$ represents a group chosen from H, OH or $C_1$–$C_6$ alkoxy, preferably methoxy.

The photosensitive screening agent from this family is preferably 2-ethylhexyl p-cinnamate, which is available commercially under the name of <<Parsol® MCX>> from Hoffmann-Laroche.

The photosensitive sunscreen agent is present in the sol in an amount ranging from 0.1% by weight up to its solubility limit in the sol, the percentage being expressed with respect to the weight of the silicon alkoxide. The photosensitive sunscreen agent is preferably present in an amount ranging from 0.1% by weight to 10% by weight with respect to the weight of the silicon alkoxide.

The solvent which is used in the present invention is preferably a linear or branched lower alcohol, better still ethanol.

The amount of solvent used in the present invention varies from 1% by weight to 85% by weight with respect to the weight of the sol.

Finally, the amount of water used in the material must be sufficient to produce complete or partial hydrolysis of the silicon alkoxide.

The pH of the water of the hydrolysis preferably lies within the range from 1 to 4, better still within the range from 1 to 2.

The present invention also relates to a photostable material comprising a photosensitive sunscreen agent combined with a photostabilizing material prepared by the sol-gel route including:

(a) at least one silicon alkoxide,
(b) at least one solvent,
(c) at least one nonionic surfactant, and
(d) water.

The term <<photostable material>> is understood to mean a material exhibiting an improved stability with respect to UV radiation.

All the (a), (b) and (d) constituents and the photosensitive sunscreen agent of the photostable material are as described above.

The nonionic surfactants which are suitable in the photostable material according to the present invention are chosen in particular from polyethoxylated, polypropoxylated or polyglycerolated fatty alcohols, alkylphenols or acids with a fatty chain comprising from 6 to 32 carbon atoms, preferably from 8 to 18 carbon atoms, the number of ethylene oxide or propylene oxide groups being between 2 and 100, preferably between 2 and 50, and the number of glycerol groups being between 2 and 30.

Mention may also be made, as nonionic surfactants, of copolymers of ethylene oxide and of propylene oxide; condensates of ethylene oxide and of propylene oxide with fatty alcohols; polyethoxylated fatty amides preferably having 2 to 30 mol of ethylene oxide; polyglycerolated fatty amides preferably comprising 1 to 5 glycerol groups and in particular 1.5 to 4; polyethoxylated fatty amines preferably having 2 to 30 mol of ethylene oxide; sorbitan fatty acid esters ethoxylated with 2 to 30 mol of ethylene oxide; sucrose fatty acid esters, polyethylene glycol fatty acid esters, alkylpolyglucosides, carbamate or amide derivatives of N-alkylglucamines, aldobionamides or amine oxides, such as alkylamine or N-(acylamidopropyl)morpholine oxides.

Preference is very particularly given, among the surfactants mentioned above, to the use of a polyethoxylated 4-(1,1,3,3-tetramethylbutyl)phenol. The latter is sold under the name of Triton® X100 by Rohm & Haas.

In order to preferably obtain the best photostabilizing effect, the constituents of the photostable material according to the invention are added in the following way. The silicon alkoxide is added to a solvent and then the following are added in the order shown below:

(1) the nonionic surfactant,
(2) the photosensitive sunscreen agent and
(3) the water.

The photostable material thus obtained can be dried and milled, and again brought into contact with another silicon alkoxide and/or a solvent and water to carry out a surface treatment of the powder. An additional layer is then obtained which further improves the stability with respect to UV radiation.

An additional subject matter of the present invention is a cosmetic and/or dermatological composition comprising, in a cosmetically and/or dermatologically acceptable vehicle, an effective amount of a photostable material according to the invention.

This cosmetic and/or dermatological composition comprises the photostable material according to the invention in an effective amount ranging from 1% by weight to 99% by weight, preferably from 1% by weight to 60% by weight, with respect to the total weight of the composition.

The cosmetic and/or dermatological composition can be provided in the form of a sol which is able to form a film and which can be applied directly to the skin to protect it against ultraviolet radiation. This application can be carried out, for example, by means of a spray.

The photostable material according to the invention is preferably dried and milled, and added in the form of particles to a cosmetic and/or dermatological composition. The mean size of the particles obtained after drying and milling the photostable material lies within the range from 0.1 to 50 $\mu$m, preferably from 0.1 to 20 $\mu$m, better still from 0.1 to 10 $\mu$m.

The cosmetic and/or dermatological compositions targeted by the present invention can, of course, comprise one or more additional sunscreen agents which are active in the UV-A region and/or UV-B region other than the photosensitive sunscreen agents defined above, these additional sunscreen agents being water soluble, fat soluble or insoluble in the cosmetic solvents commonly used. These additional screening agents can be chosen in particular from salicylic derivatives, camphor derivatives, triazine derivatives, such as those disclosed in Patent Applications U.S. Pat. No. 4,367,390, EP 0 863 145, EP 0 517 104, EP 0 570 838, EP 0 796 851, EP 0 775 698, EP 0 878 469, EP 0 933 376 and EP 0 893 119, benzophenone derivatives, $\beta,\beta'$-diphenylacrylate derivatives, benzimidazole derivatives, methylenebis(hydroxyphenylbenzotriazole) derivatives, such as those disclosed in Patent Applications U.S. Pat. No. 5,237,071, U.S. Pat. No. 5,166,355, GB 2 303 549, DE 19726184 and EP 0 893 119, p-aminobenzoic acid derivatives, the screening hydrocarbonaceous and screening silicone polymers disclosed in Application WO-93/04665, and bis(benzoazolyl) derivatives, such as those disclosed in Patent Application [sic] EP 0 669 323 and U.S. Pat. No. 2,463,264.

Mention may be made, as examples of additional sunscreen agents which are active in the UV-A region and/or the UV-B region, of:

p-aminobenzoic acid,
ethoxylated (25 mol) p-aminobenzoate,
2-ethylhexyl p-dimethylaminobenzoate,
N-propoxylated ethyl p-aminobenzoate,
glycerol p-aminobenzoate,
homomenthyl salicylate,
2-ethylhexyl salicylate,
triethanolamine salicylate,
4-isopropylbenzyl salicylate,
menthyl anthranilate,
2-ethylhexyl 2-cyano-3,3-diphenylacrylate,
ethyl 2-cyano-3,3-diphenylacrylate,
2-phenylbenzimidazole-5-sulfonic acid and its salts, 3-((4'-trimethylammonium)benzylidene)bornan-2-one [sic] methyl sulfate, 2-hydroxy-4-methoxybenzophenone, 2-hydroxy-4-methoxybenzophenone-5-sulfonate [sic], 2,4-dihydroxybenzophenone, 2,40,4,4'-tetrahydroxybenzophenone, 2,2'-dihydroxy-4,4'-dimethoxybenzophenone, 2-hydroxy-4-(n-octoxy)benzophenone, 2-hydroxy-4-methoxy-4'-methylbenzophenone, α-(2-oxoborn-3-ylidene)tolyl-4-sulfonic [sic] acid and its salts, 3-((4'-sulfo)benzylidene)bornan-2-one [sic] and its salts, 3-(4'-methylbenzylidene)-d,l-camphor, 3-benzylidene-d,l-camphor, urocanic acid, 2,4,6-tris[p-(2'-ethylhexyl-1'-oxycarbonyl)anilino]-1,3,5-triazine, 2-[(p-(tert-butylamido)anilino]-4,6-bis[(p-(40-ethylhexyl-1'-oxycarbonyl)anilino]-1,3,5-triazine [sic], 2,4-bis{[4-(2-ethylhexyloxy)-2-hydroxy]phenyl}-6-(4-methoxyphenyl)-1,3,5-triazine [sic] (Tinosorb®, Ciba-Geigy), the polymer of N-(2- and 4-)[(2-oxoborn-3-ylidene)-methyl)benzyl]acrylamide, 1,4-bis(benzimidazolyl)phenylene-3,31,5,51-tetrasulfonic acid and its soluble salts, polyorganosiloxanes comprising a benzalmalonate functional group, polyorganosiloxanes comprising a benzotriazole function, such as drometrizole trisiloxane,

[2,2'-methylenebis[6-(2H-benzotriazol-2-yl)-4-(1,1,3,3-tetramethylbutyl)phenol] [sic] in the dissolved form, such as the product sold under the name Mixxim® BB/100 by Fairmount Chemical, or else in insoluble micronized form, such as the product sold under the name Tinosorb® M by Ciba-Geigy,

[2,2'-methylenebis[6-(2H-benzotriazol-2-yl)-4-(methyl)phenol] [sic] in the dissolved form, such as the product sold under the name Mixxim® BB/200 by Fairmount Chemical.

The compositions according to the invention can also comprise agents for the artificial tanning and/or browning of the skin (self-tanning agents), such as, for example, dihydroxyacetone (DHA).

The cosmetic and/or dermatological compositions according to the invention can also comprise pigments or alternatively nanopigments (mean size of the primary particles, in general between 5 nm and 100 nm, preferably between 10 and 50 nm) formed of coated or uncoated metal oxides, such as, for example, nanopigments formed of titanium oxide (amorphous or crystalline in the rutile and/or anatase form), iron oxide, zinc oxide, zirconium oxide or cerium oxide which are all photoprotective agents well known per se which act by physical blocking (reflection and/or scattering) of UV radiation. Conventional coating agents are, furthermore, alumina and/or aluminum stearate. Such nanopigments formed of coated or uncoated metal oxides are disclosed in particular in Patent Applications EP-A-0 518 772 and EP-A-0 518 773.

The compositions in accordance with the present invention can additionally comprise conventional cosmetic adjuvants chosen in particular from fatty substances, organic solvents, ionic or nonionic thickeners, softeners, antioxidants, agents for combating free radicals, opacifiers, stabilizers, emollients, silicones, (α-hydroxy acids, anti-foaming agents, moisturizing agents, vitamins, fragrances, preservatives, surfactants, fillers, sequestering agents, polymers, propellants, basifying or acidifying agents, dyes or any other ingredient commonly used in the cosmetics and/or dermatological field, in particular for the manufacture of antisun compositions in the form of emulsions.

The fatty substances can be composed of an oil or a wax or their mixtures. The term <<oil>> is understood to mean a compound which is liquid at ambient temperature. The term <<wax>> is understood to mean a compound which is solid or substantially solid at ambient temperature and which has a melting point generally of greater than 350° C.

Mention may be made, as oils, of mineral oils (liquid petrolatum); vegetable oils (sweet almond, macadamia, blackcurrant seed or jojoba oil); synthetic oils, such as perhydrosqualene, fatty alcohols, acids or esters (such as the benzoate $C_{12}$–$C_{15}$ alcohols sold under the name <<Finsolv TN>> by Finetex, octyl palmitate, isopropyl lanolate or triglycerides, including those of capric/caprylic acids), or ethoxylated or propoxylated fatty esters and ethers; silicone oils (cyclomethicone, preferably comprising 4 or 5 silicon atoms, or polydimethylsiloxane or PDMS); fluorinated oils; or polyalkylenes.

Mention may be made, as waxy compounds, of paraffin wax, carnauba wax, beeswax or hydrogenated castor oil.

Mention may be made, among organic solvents, of lower alcohols and polyols.

The thickeners can be chosen in particular from crosslinked polyacrylic acids, modified or unmodified guar and cellulose gums, such as hydroxypropylated guar gum, methylhydroxyethylcellulose or hydroxypropylmethylcellulose, and silicone gums, such as, for example, a polydimethylsiloxane derivative.

The cosmetic and/or dermatological compositions according to the invention can be prepared according to techniques well known to a person skilled in the art, in particular those intended for the preparation of emulsions of oil-in-water or water-in-oil type.

This cosmetic and/or dermatological composition can be provided in particular in the form of a simple or complex emulsion (O/W, W/O, O/W/O or W/O/W), such as a cream or a milk, or in the form of a gel or a cream gel, of a powder or of a solid stick and can optionally be packaged in an aerosol and be provided in the form of a foam or a spray.

The cosmetic and/or dermatological compositions according to the invention are preferably provided in the form of an oil-in-water emulsion.

When it is an emulsion, the aqueous phase of the latter can comprise a nonionic vesicular dispersion prepared according to known processes (Bangham, Standish and Watkins, J. Mol. Biol., 13, 238 (1965), FR 2 315 991 and FR 2 416 008).

The cosmetic and/or dermatological composition according to the invention is used as composition for protecting the skin or keratinous substances against ultraviolet rays, as antisun composition or as makeup product.

When the cosmetic composition according to the invention is used for protecting the hair, it can be provided in the form of a shampoo, lotion, gel, emulsion or nonionic vesicular dispersion and can constitute, for example, a rinse-out composition, to be applied before or after shampooing, before or after dyeing or bleaching or before, during or after perming or hair straightening, a styling or treating lotion or gel, a lotion or a gel for blow drying or hairsetting, or a composition for perming or straightening or for dyeing or bleaching the hair.

EXAMPLE 1

A material is synthesized by the sol-gel route from:

| | |
|---|---|
| Tetraethoxysilane (TEOS) | 1.8 g |
| Absolute ethanol | 13.6 g |
| Water (0.01N HCl) | 1.0 g |
| Triton ® X-100 | 0.6 g |
| Parsol ® 1789 | 0.04 g | the tetraethoxysilane originating from Fluka, the Parsol® 1789 being sold by Hoffmann-Laroche and the Triton® X-100 being sold by Rohm & Haas.

The TEOS is added to the ethanol with stirring. The Triton® X-100 is subsequently added with stirring, followed by the Parsol® 1789, still with stirring. No incompatibility between the components was observed. The mixture is stirred for 5 minutes. The water (0.01N HCl) is added and the mixture is stirred for 60 minutes at 30° C. The mixture is allowed to return to ambient temperature with stirring. The material is ready for use.

EXAMPLE 2

A material is synthesized by the sol-gel route from:

| | |
|---|---|
| Tetraethoxysilane (TEOS) | 1.8 g |
| Absolute ethanol | 14.43 g |
| Water (0.1N HCl) | 1.5 g |
| Triton ® X-100 | 0.6 g |
| Parsol ® 1789 | 0.05 g |
| Methyltriethoxysilane (MTES) | 3.2 g | the tetraethoxysilane originating from Fluka, the Parsol® 1789 being sold by Hoffmann-Laroche, the Triton® X-100 being sold by Rohm & Haas and the methyltriethoxysilane being sold by Interchim.

The TEOS is added to the ethanol with stirring. The Triton® X-100 is subsequently added with stirring, followed by the Parsol® 1789, still with stirring. The mixture is stirred for 5 minutes. Water (0.01N HCl) is added and the mixture is stirred for 30 minutes at 48° C. The mixture is allowed to return to ambient temperature with stirring. The sol thus obtained is placed in a ventilated oven at 50° C. for 24 hours. A white solid is then obtained, which solid is milled in order to obtain a white powder.

Furthermore, a sol is prepared from the MTES. For this, the MTES, the ethanol and the water are mixed at ambient temperature and the mixture is stirred for 1 hour at ambient temperature. Subsequently, 500 mg of the powder obtained above are dissolved in this sol prepared from MTES. This novel sol comprising powder is ready for use.

Tests of Stability with Respect to UV Radiation

Tests of stability with respect to UV radiation of Parsol® 1789 were subsequently carried out by irradiating the materials obtained in Examples 1 and 2 and, by way of comparison, materials comprising Parsol® 1789 but without surfactant.

The materials are deposited on glass sheets (microscope slides). Films are formed on the sheets after evaporation of the volatile components of the mixture. The drying time of the films is fast, that is to say between 1 and 3 minutes.

The films obtained are then irradiated under the following conditions:

Energy of the UV-A lamp=19 mW/cm$^2$,
Energy of the UV-B lamp=0.6 mW/cm$^2$,
Irradiation time=20 minutes.

These conditions correspond to approximately 1 hour of sunshine.

The photodecomposition is monitored by absorption spectrophotometry or by HPLC. The results are combined in the following table.

TABLE

| Materials studied | Film formation | Photodecomposition after irradiating for 20 minutes |
|---|---|---|
| TEOS | no | — |
| MTES/TEOS 40/60 (in mol) | yes | 70% |
| MTMS | yes | 55% |
| TEOS/3.7% Triton ® X-100 (Example 1) | yes | 25% (±2%) |
| TEOS/3.7% Triton ® X-100/MTES (Example 2) | yes | 20% (±2%) |

MTMS: methyltrimethoxysilane.

From this table, the materials according to the present invention exhibit better stability with respect to UV radiation in comparison with the materials not comprising surfactant. Furthermore, all the materials studied were observed to be persistent toward pure or salt water and toward polar and nonpolar cosmetic oils.

What is claimed is:

1. A process for improving the stability with respect to UV radiation of a photosensitive sunscreen agent, wherein the process comprises the incorporation of said sunscreen agent in a photostabilizing material prepared by sol-gel route from at least one silicon alkoxide and at least one non-ionic surfactant.

2. The process of claim 1, wherein the photostabilizing material prepared by the sol-gel route comprises at least one silicon alkoxide, at least one surfactant, at least one solvent and water.

3. The process of claim 1, wherein the silicon alkoxide has a formula corresponding to one of the following formulae:

$$Si(OR_1)_4 \qquad (I)$$

$$R-Si(OR_1)_3 \qquad (II)$$

$$(R_1O)_3-Si-R''-Si(OR_1)_3 \qquad (III)$$

$$R-\underset{R'}{\underset{|}{Si(OR_1)_2}} \qquad (IV)$$

wherein:
   $R_1$ represents a linear or branched $C_{1-30}$ alkyl group;
   R and R', independently of one another, represent a linear or branched alkyl group, a cycloalkyl group or an aryl group which is substituted or unsubstituted;
   R" represents a linear or branched alkylene group, a cycloalkylene group or an arylene group which is substituted or unsubstituted.

4. The process of claim 3, wherein $R_1$ is linear or branched $C_{1-6}$ alkyl group.

5. The process of claim 3, wherein R, R' and/or R" further comprises a cosmetically or dermatologically active group.

6. The process of claim 1, wherein the silicon alkoxide is selected from the group consisting of tetraethoxysilane and methyltriethoxysilane.

7. The process of claim 1, wherein the nonionic surfactant is selected from the group consisting of polyethoxylated, polypropoxylated and polyglycerolated fatty alcohols, alkylphenols and acids with a fatty chain comprising from 6 to 32 carbon atoms, the number of ethylene oxide or propylene oxide groups being between 2 and 100 and the number of glycerol groups being between 2 and 30; copolymers of ethylene oxide and of propylene oxide; condensates of ethylene oxide and of propylene oxide with fatty alcohols; polyethoxylated fatty amides; polyglycerolated fatty amides; polyethoxylated fatty amines; ethoxylated sorbitan fatty acid esters; sucrose and polyethylene glycol fatty acid esters; alkylpolyglucosides; amide or carbamate derivatives of N-alkylglucamine, aldobionamides and amine oxides.

8. The process of claim 1, wherein the surfactant is a polyethoxylated 4-(1,1,3,3-tetramethylbutyl)phenol.

9. The process of claim 1, wherein the surfactant is present in an amount from 0.01% to 99% by weight with respect to the silicon alkoxide.

10. The process of claim 1, wherein the surfactant is present in an amount from 10% to 60% by weight with respect to the silicon alkoxide.

11. The process of claim 1, wherein the photosensitive sunscreen agent is selected from the group consisting of dibenzoylmethane derivatives and cinnamic acid derivatives.

12. The process of claim 1, wherein the photosensitive sunscreen agent is selected from the group consisting of:
2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4,4'-dimethoxydibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane, and
2,6-dimethyl-4-tert-butyl-4'-methoxydibenzoylmethane.

13. The process of claim 1, wherein the photosensitive sunscreen agent is 4-tert-butyl-4'-methoxydibenzoylmethane.

14. The process of claim 1, wherein the photosensitive sunscreen agent is chosen from cinnamic acid derivatives corresponding to the following general formula:
wherein A represents:

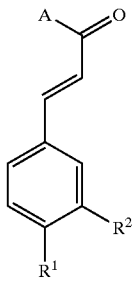

an $OR^3$ group, $R^3$ being selected from the group consisting hydrogen atom, a phytyl or benzyl group, a saturated or unsaturated and linear, branched or cyclic $C_1$–$C_{18}$ alkyl group, an alkali metal or an alkaline earth metal salt or an ammonium ion, or an $NHR^4$ group, wherein $R^4$ is a hydrogen atom, a phytyl or benzyl group or a saturated or unsaturated, linear, branched or cyclic $C_1$–$C_{18}$ alkyl group;

$R^1$ represents a group selected from the group consisting of H, OH, $C_1$–$C_6$ alkoxy, and saturated, unsaturated, linear, branched and cyclic $C_1$–$C_{18}$ alkyl groups;

$R^2$ represents a group chosen from H, OH or $C_1$–$C_6$ alkoxy.

15. The process of claim 14, wherein R1 and/or R2 are methoxy.

16. The process of claim 14, wherein the photosensitive sunscreen agent is 2-ethylhexyl p-cinnamate.

17. The process of claim 1, wherein the photosensitive sunscreen agent is present in an amount ranging from 0.1% by weight up to its solubility limit in sol with respect to the weight of the silicon alkoxide.

18. The process of claim 1, wherein the photosensitive sunscreen agent is present in an amount ranging from 0.1% by weight to 10% by weight with respect to the total weight of the silicon alkoxide.

19. The process of claim 2, wherein the solvent is an alcohol.

20. The process of claim 19, wherein the alcohol is a linear or branched lower alcohol.

21. The process of claim 20, wherein the alcohol is ethanol.

22. The process of claim 2, wherein the solvent is present in an amount from 1 to 85% by weight with respect to the total weight of the material.

23. The process of claim 1, wherein the sol gel route comprises hydrolysis conducted in water corresponding to a pH of from 1 to 4.

24. The process of claim 23, wherein the hydrolysis is conducted in water corresponding to a pH of from 1 to 2.

25. A photostable material comprising a photosensitive sunscreen agent combined with a photostabilizing material prepared by sol-gel route and comprising:
(a) at least one silicon alkoxide,
(b) at least one solvent,
(c) at least one nonionic surfactant, and
(d) water.

26. The photostable material of claim 25, wherein the silicon alkoxide has a formula corresponding to one of the following formulae:

 (I)
 (II)
 (III)

(IV)

wherein:
$R_1$ represents a linear or branched $C_{1-30}$ alkyl group;
R and R', independently of one another, represent a linear or branched alkyl group, a cycloalkyl group or an aryl group which is substituted or unsubstituted;
R" represents a linear or branched alkylene group, a cycloalkylene group or an arylene group which is substituted or unsubstituted.

27. The photostable material of claim 26, wherein $R_1$ is linear or branched $C_{1-6}$ alkyl group.

28. The photostable material of claim 26, wherein R, R' and/or R" further comprises a cosmetically or dermatologically active group.

29. The photostable material of claim 25, wherein the silicon alkoxide is selected from the group consisting of tetraethoxysilane and methyltriethoxysilane.

30. The photostable material of claim 25, wherein the surfactant is a nonionic surfactant.

31. The photostable material of claim 30, wherein the nonionic surfactant is selected from the group consisting of polyethoxylated, polypropoxylated and polyglycerolated fatty alcohols, alkylphenols and acids with a fatty chain comprising from 6 to 32 carbon atoms, the number of ethylene oxide or propylene oxide groups being between 2 and 100 and the number of glycerol groups being between 2 and 30; copolymers of ethylene oxide and of propylene oxide; condensates of ethylene oxide and of propylene oxide with fatty alcohols; polyethoxylated fatty amides; polyglycerolated fatty amides; polyethoxylated fatty amines; ethoxylated sorbitan fatty acid esters; sucrose and polyethylene glycol fatty acid esters; alkylpolyglucosides; amide or carbamate derivatives of N-alkylglucamine, aldobionamides and amine oxides.

32. The photostable material of claim 25, wherein the surfactant is a polyethoxylated 4-(1,1,3,3-tetramethylbutyl) phenol.

33. The photostable material of claim 25, wherein the photosensitive sunscreen agent is selected from the group consisting of dibenzoylmethane derivatives and cinnamic acid derivatives.

34. The photostable material of claim 25, wherein the photosensitive sunscreen agent is selected from the group consisting of:

2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, and 2,6-dimethyl-4-tert-butyl-4'-methoxydibenzoylmethane.

35. The photostable material of claim 25, wherein the photosensitive sunscreen agent is 4-tert-butyl-4'-methoxydibenzoylmethane.

36. The photostable material of claim 25, wherein the photosensitive sunscreen agent is chosen from cinnamic acid derivatives corresponding to the following general formula:

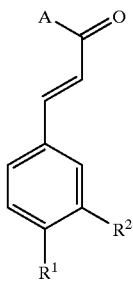

wherein A represents:

an $OR^3$ group, $R^3$ being selected from the group consisting hydrogen atom, a phytyl or benzyl group, a saturated or unsaturated and linear, branched or cyclic $C_1$–$C_{18}$ alkyl group, an alkali metal or an alkaline earth metal salt or an ammonium ion, or an $NHR^4$ group, wherein $R^4$ is a hydrogen atom, a phytyl or benzyl group or a saturated or unsaturated, linear, branched or cyclic $C_1$–$C_{18}$ alkyl group;

$R^1$ represents a group selected from the group consisting of H, OH, $C_1$–$C_6$ alkoxy, and saturated, unsaturated, linear, branched and cyclic $C_1$–$C_{18}$ alkyl groups;

$R^2$ represents a group chosen from H, OH or $C_1$–$C_6$ alkoxy, preferably methoxy.

37. The photostable material of claim 36, wherein R1 and/or R2 are methoxy.

38. The photostable material of claim 25, wherein the photosensitive sunscreen agent is 2-ethylhexyl p-cinnamate.

39. The photostable material of claim 25, wherein the solvent is an alcohol.

40. The photostable material of claim 39, wherein the alcohol is a linear or branched lower alcohol.

41. The photostable material of claim 40, wherein the alcohol is ethanol.

42. The photostable material of claim 25, wherein the silicon alkoxide is added to a solvent and then, in the following order, the nonionic surfactant, the photosensitive sunscreen agent and the water are added.

43. The photostable material of claim 42, wherein the material is dried and milled, and brought into contact with another silicon alkoxide and/or a solvent and water.

44. A cosmetic and/or dermatological composition comprising a screening agent which is photosensitiveto UV radiation and an effective amount of the photostable material of claim 25 in cosmetically and/or dermatologically acceptable vehicle.

45. The cosmetic and/or dermatological composition of claim 44, further comprising an additive selected from the group consisting of sunscreen agents other than photosensitive sunscreen agents, agents for the artificial tanning and/or browning of the skin, pigments, fatty substances, organic solvents, thickeners, softeners and antioxidants.

46. The cosmetic and/or dermatological composition of claim 44, wherein the photostable material is added in an effective amount ranging from 1% by weight to 99% by weight, with respect to the total weight of the cosmetic and/or dermatological composition.

47. The cosmetic and/or dermatological composition of claim 44, wherein the photostable material is added in an effective amount ranging from 10% by weight to 60% by weight, with respect to the total weight of the cosmetic and/or dermatological composition.

48. The cosmetic and/or dermatological composition of claim 44, wherein the photostable material is in the form of particles obtained by drying and milling.

49. The cosmetic and/or dermatological composition of claim 48, wherein the mean size of the particles obtained by drying and milling the photostable material is from 0.1 to 50 μm.

50. The cosmetic and/or dermatological composition of claim 48, wherein the mean size of the particles obtained by drying and milling the photostable material is from 0.1 to 20 μm.

* * * * *